US00PP29811P2

(12) United States Plant Patent
Hofmann

(10) Patent No.: US PP29,811 P2
(45) Date of Patent: Nov. 6, 2018

(54) ***PETUNIA* PLANT NAMED 'INPETROYMA'**

(50) Latin Name: *Petunia X hybrida*
Varietal Denomination: INPETROYMA

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 15/731,896

(22) Filed: Aug. 21, 2017

(51) Int. Cl.
*A01H 5/02* (2018.01)

(52) U.S. Cl.
USPC ..... Plt./356.21
CPC ..... *A01H 5/02* (2013.01)

(58) Field of Classification Search
USPC ..... Plt./356.21, 356.22
CPC ..... A01H 5/02
See application file for complete search history.

*Primary Examiner* — Kent L Bell
(74) *Attorney, Agent, or Firm* — C. A. Whealy

(57) ABSTRACT

A new and distinct *Petunia* plant named 'INPETROYMA', characterized by its compact, outwardly spreading and mounding to eventually trailing plant habit; freely branching habit; moderately vigorous growth habit; early and freely flowering habit; large dark red purple-colored flowers with dark purple-colored venation and throats; and good garden performance.

1 Drawing Sheet

Botanical designation: *Petunia* X *hybrida.*
Cultivar denomination: 'INPETROYMA'.

BACKGROUND OF THE INVENTION

The present invention relates to a new and distinct cultivar of *Petunia* plant, botanically known as *Petunia* X *hybrida* and hereinafter referred to by the name 'INPETROYMA'.

The new *Petunia* plant is a product of a planned breeding program conducted by the Inventor in Johannesburg, South Africa and Heidesheim, Germany. The objective of the breeding program is to create new freely-branching and uniformly mounding *Petunia* plants with early and freely flowering habit, unique attractive flowers and good garden performance.

The new *Petunia* plant originated from a cross-pollination made by the Inventor in December, 2013 in Johannesburg, South Africa of *Petunia* X *hybrida* 'Sunremi', disclosed in U.S. Plant Pat. No. 16,803, as the female, or seed, parent and *Petunia* X *hybrida* 'USTUNI8902', disclosed in U.S. Plant Pat. No. 17,895, as the male, or pollen, parent. The new *Petunia* plant was discovered and selected by the Inventor as a single flowering plant within the progeny of the stated cross-pollination in a controlled greenhouse environment in Heidesheim, Germany in July, 2014.

Asexual reproduction of the new *Petunia* plant by vegetative terminal cuttings in a controlled greenhouse environment in Heidesheim, Germany since August, 2014 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INPETROYMA'. These characteristics in combination distinguish 'INPETROYMA' as a new and distinct *Petunia* plant:

1. Compact, outwardly spreading and mounding to eventually trailing plant habit.
2. Freely branching habit.
3. Moderately vigorous growth habit.
4. Early and freely flowering habit.
5. Large dark red purple-colored flowers with dark purple-colored venation and throats.
6. Good garden performance.

Plants of the new *Petunia* can be compared to plants of the female parent, 'Sunremi'. In side-by-side comparisons, plants of the new *Petunia* differ primarily from plants of 'Sunremi' in the following characteristics:

1. Plants of the new *Petunia* are more trailing than and not as upright as 'Sunremi'.
2. Plants of the new *Petunia* and 'Sunremi' differ in flower color as plants of 'Sunremi' have red-colored flowers.

Plants of the new *Petunia* can be compared to plants of the male parent, 'USTUNI8902'. In side-by-side comparisons, plants of the new *Petunia* differ primarily from plants of 'USTUNI8902' in the following characteristics:

1. Plants of the new *Petunia* are more compact than plants of 'USTUNI8902'.
2. Plants of the new *Petunia* flower earlier than plants of 'USTUNI8902'.
3. Plants of the new *Petunia* and 'USTUNI8902' differ in flower color as plants of 'USTUNI8902' have brighter and more reddish-colored flowers.

Plants of the new *Petunia* can be compared to plants of 'Kakegawa S36', disclosed in U.S. Plant Pat. No. 14,037. In side-by-side comparisons, plants of the new *Petunia* differ primarily from plants of 'Kakegawa S36' in the following characteristics:

1. Plants of the new *Petunia* are more freely branching than plants of 'Kakegawa S36'.
2. Leaves of plants of the new *Petunia* are smaller than leaves of plants of 'Kakegawa S36'.
3. Plants of the new *Petunia* are more freely flowering than plants of 'Kakegawa S36'.
4. Flowers of plants of the new *Petunia* are slightly smaller than flowers of plants of 'Kakegawa S36'.

Plants of the new *Petunia* can also be compared to plants of 'Kakegawa S28', disclosed in U.S. Plant Pat. No. 13,887. In side-by-side comparisons, plants of the new *Petunia* differ primarily from plants of 'Kakegawa S28' in the following characteristics:

1. Plants of the new *Petunia* are more freely branching than plants of 'Kakegawa S28'.
2. Plants of the new *Petunia* are more freely flowering than plants of 'Kakegawa S28'.
3. Plants of the new *Petunia* and 'Kakegawa S28' differ in flower color as plants of 'Kakegawa S28' have dark purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet is a side perspective view of a typical flowering plant of 'INPETROYMA' grown in a container.

The photograph at the top of the sheet is a close-up view of a typical flowering plant of 'INPETROYMA'.

DETAILED BOTANICAL DESCRIPTION

The aforementioned photographs and following observations and measurements describe plants grown during the early spring in 11.5-cm containers in an acrylic-covered greenhouse in Carleton, Mich. and under cultural practices typical of commercial *Petunia* production. During the production of the plants, day and night temperatures ranged from 18° C. to 27° C. Plants were eleven weeks from planting rooted cuttings when the photographs and description were taken. In the following description, color references are made to The Royal Horticultural Society Colour Chart, 2007 Edition, except where general terms of ordinary dictionary significance are used.

Botanical classification: *Petunia* X *hybrida* 'INPETROYMA'.

Parentage:

*Female, or seed, parent.*—*Petunia* X *hybrida* 'Sunremi', disclosed in U.S. Plant Pat. No. 16,803.

*Male, or pollen, parent.*—*Petunia* X *hybrida* 'USTUNI8902', disclosed in U.S. Plant Pat. No. 17,895.

Propagation:

*Type.*—Terminal vegetative cuttings.

*Time to initiate roots, summer.*—About three to four days at temperatures ranging from 17° C. to 29° C.

*Time to initiate roots, winter.*—About five to seven days at temperatures ranging from 17° C. to 21° C.

*Time to produce a rooted plant, summer.*—About three weeks at temperatures ranging from 17° C. to 29° C.

*Time to produce a rooted plant, winter.*—About four weeks at temperatures ranging from 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, outwardly spreading and mounding to eventually trailing plant habit; freely branching habit with about three to four primary lateral branches with numerous secondary and tertiary lateral branches per primary lateral branch developing; dense and bushy appearance; pinching enhances development of lateral branches; moderately vigorous growth habit.

*Plant height, soil level to top of foliar plane.*—About 10.5 cm.

*Plant height, soil level to top of floral plane.*—About 13 cm.

*Plant diameter* (*area of spread*).—About 32.5 cm.

*Lateral branches.*—Length: About 20 cm. Diameter: About 2.5 mm. Internode length: About 1.6 cm. Strength: Strong. Aspect: Initially upright then outwardly spreading to trailing. Texture and luster: Pubescent; matte. Color, developing: Close to 146B. Color, developed: Close to 146A.

Leaf description:

*Arrangement.*—Alternate before flowering; opposite after flowers develop; leaves simple.

*Length.*—About 5 cm.

*Width.*—About 2.5 cm.

*Shape.*—Elliptical.

*Apex.*—Broadly acute.

*Base.*—Attenuate.

*Margin.*—Entire.

*Texture and luster, upper and lower surfaces.*—Minute pubescence; matte.

*Venation pattern.*—Pinnate, arcuate.

*Color.*—Developing leaves, upper surface: Close to 146A. Developing leaves, lower surface: Close to 146B. Fully expanded leaves, upper surface: Close to N137A; venation, close to 146C. Fully expanded leaves, lower surface: Close to 146B; venation, close to 146C.

*Petioles.*—Length: About 1.1 cm. Diameter: About 3 mm. Strength: Moderately strong. Texture and luster, upper and lower surfaces: Scattered pubescence; matte. Color, upper and lower surfaces: Close to 146C.

Flower description:

*Flower type and flowering habit.*—Single axillary salverform flowers; flowers face mostly upward to outwardly; freely flowering habit with about 45 flowers and flower buds per plant.

*Natural flowering season.*—Long day responsive; long flowering period, plants flower from spring until frost in the autumn, flowering continuous during this period; early flowering habit, plants begin flowering about six weeks after planting.

*Flower longevity on the plant*.—About four to five days; flowers persistent.

*Fragrance*.—None detected.

*Flower buds*.—Length: About 3.2 cm. Diameter: About 6 mm. Shape: Oblong, elongate. Texture and luster: Pubescent; matte. Color: Close to 76B.

*Flower diameter*.—About 4 cm by 5.5 cm.

*Flower depth (height)*.—About 4 cm.

*Throat diameter, distal*.—About 1 cm by 1.2 cm.

*Tube length*.—About 3.2 cm.

*Tube diameter*.—About 9 mm.

*Petals*.—Quantity and arrangement: Five petals fused in a single salverform whorl. Petal lobe length (from throat): About 2.2 cm. Petal lobe width: About 2.5 cm. Petal lobe shape: Fan-shaped. Petal lobe apex: Broadly acute with a shallow central point. Petal lobe margin: Entire, slightly undulate. Petal lobe texture and luster, upper surface: Smooth, glabrous; velvety; matte. Petal lobe texture and luster, lower surface: Moderately pubescent; matte. Throat texture and luster: Smooth, glabrous; matte. Tube texture and luster: Minute pubescence; matte. Color: When opening, upper surface: Close to 71B. When opening, lower surface: Close to 75A to 75B. Fully opened, upper surface: Close to 71A; venation, close to N79B; color becoming closer to 71C to 71D with development. Fully opened, lower surface: Close to 77C to 77D; venation, close to 146C; color becoming closer to 76B to 76C development. Flower throat (inside): Close to N79B; venation, close to N77D. Flower tube (outside): Close to N79A; venation, close to 148B.

*Sepals*.—Quantity and arrangement: Five sepals fused in a single star-shaped whorl. Calyx length: About 1.8 cm. Calyx diameter: About 3 cm. Length: About 1.5 cm. Width: About 2 mm. Shape: Ligulate. Apex: Rounded. Margin: Entire. Texture and luster, upper and lower surfaces: Pubescent; matte. Color: When opening and fully opened, upper surface: Close to 137A. When opening and fully opened, lower surface: Close to 137B.

*Peduncles*.—Length: About 3 cm. Width: About 1.5 mm. Strength: Strong. Angle: About 45° to 55° from the stem axis. Texture and luster: Pubescent; matte. Color: Close to 146A.

*Reproductive organs*.—Stamens: Quantity per flower: Five. Filament length: About 7 mm. Filament color: Close to 145D. Anther size: About 1.5 mm by 1 mm. Anther shape: Round. Anther color: Close to 202C. Pollen amount: Moderate. Pollen color: Slightly more grey and duller than N92D. Pistils: Quantity per flower: One. Pistil length: About 2 cm. Style length: About 1.7 cm. Style color: Close to 197C. Stigma diameter: About 2 mm. Stigma shape: Round. Stigma color: Close to 197B. Ovary color: Close to 144A.

*Seeds and fruits*.—Seed and fruit development has not been observed on plants of the new *Petunia* to date.

Pathogen & pest resistance: Plants of the new *Petunia* have not been noted to be resistant to pathogens or pests common to *Petunia* plants to date.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'INPETROYMA' as illustrated and described.

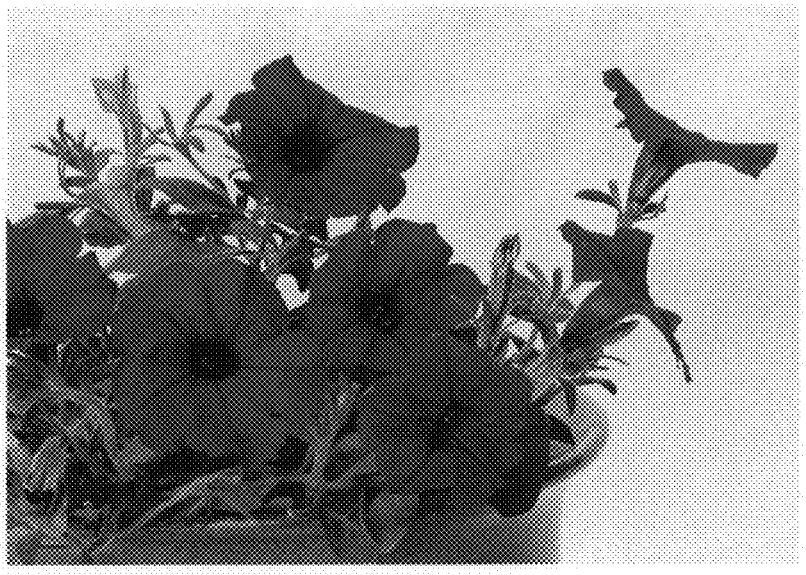
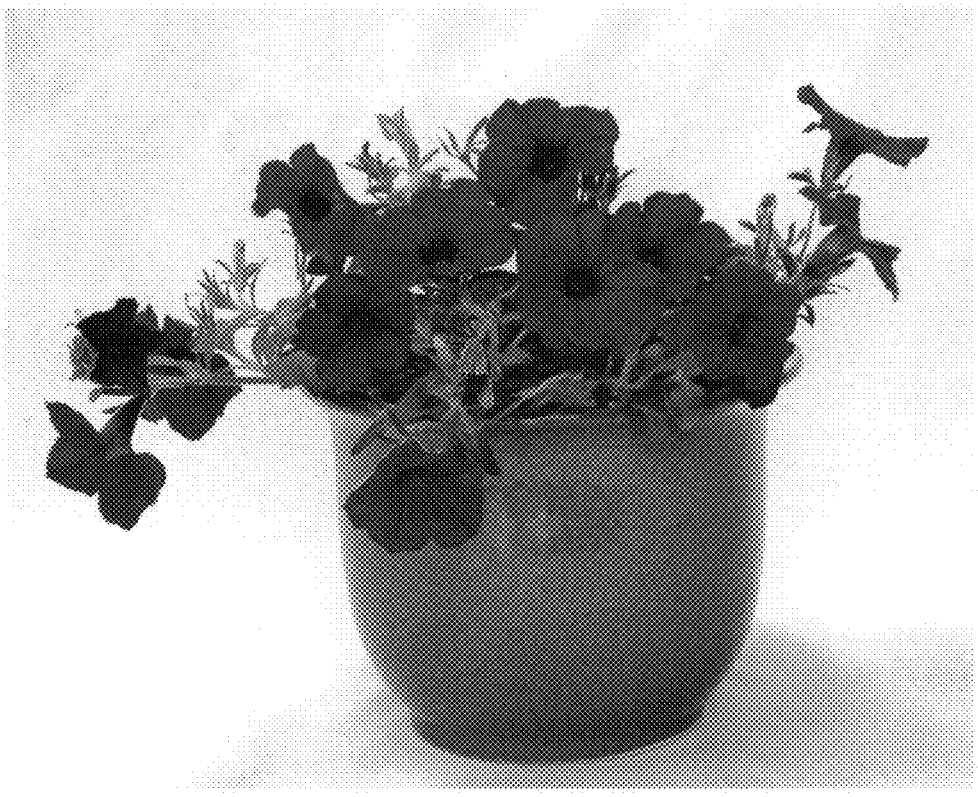

* * * * *